United States Patent [19]

Tyihak et al.

[11] Patent Number: 4,658,000

[45] Date of Patent: Apr. 14, 1987

[54] POLYACRYLAMIDE ADHESIVE FOR FIXING THE SORBENT LAYERS OF OVERPRESSURED, ONE-AND MULTILAYER-CHROMATOGRAPHIC PLATES AND A PROCESS FOR THE PREPARATION THEREOF

[75] Inventors: Erno Tyihak, Budapest; Emil Mincsovics, Szentendre; Sandor Zoltan; Gabor Kemeny, both of Budapest; Aniko Mathuny, Esztergom; Tibor Szekely, Budapest; Sandor Nemeth, Budapest; Zsuzsanna Antal, Budapest; Zsuzsanna Fater, Jaszapati, all of Hungary

[73] Assignees: Reanal Finomvegyszergyar, Budapest; "Labor" Muszeripari Muvek, Esztergom, both of Hungary

[21] Appl. No.: 641,439

[22] Filed: Aug. 16, 1984

[30] Foreign Application Priority Data

Aug. 16, 1983 [HU] Hungary .............................. 2875/83

[51] Int. Cl.⁴ ...................... C08F 2/10; C08F 222/38; C09J 3/14
[52] U.S. Cl. ................................... 526/217; 526/229; 526/229.5; 526/303.1; 526/306; 524/829; 528/493; 528/496; 528/502; 156/331.8; 210/656
[58] Field of Search .................. 526/306, 303.1, 229.5, 526/229, 217, 307.2; 210/656, 198.2, 198.3; 524/827, 829; 523/332; 528/493, 495, 502; 156/331.8

[56] References Cited

U.S. PATENT DOCUMENTS

| | | | |
|---|---|---|---|
| 3,061,595 | 10/1962 | Dorion et al. | 526/306 X |
| 3,200,098 | 8/1965 | Goren | 526/229.5 |
| 3,535,265 | 10/1970 | Baron et al. | 210/198.3 X |
| 3,922,431 | 11/1975 | Radmacher et al. | 428/327 |
| 4,074,039 | 2/1978 | Lim et al. | 526/307.2 X |
| 4,111,922 | 9/1978 | Beede et al. | 526/306 X |
| 4,254,249 | 3/1981 | Cottrell et al. | 526/303 |

FOREIGN PATENT DOCUMENTS

0914567  3/1982  U.S.S.R. .............................. 524/827

*Primary Examiner*—Joseph L. Schofer
*Assistant Examiner*—F. M. Teskin
*Attorney, Agent, or Firm*—Karl F. Ross; Herbert Dubno

[57] ABSTRACT

The invention relates to a new polyacrylamide adhesive suitable for the fixing of fine-particle sorbent layers based on organic and/or inorganic compounds, used in overpressured one- and multilayer chromatographic procedures.

The said adhesive is prepared by polymerizing the aqueous solutions of acrylamide and N,N'-methylene-bis-acrylamide in the presence of a catalyst pair at from 21° to 30° C., pulpifying the precipitate thus obtained and repeating the precipitation and the pulpification more times.

10 Claims, No Drawings

POLYACRYLAMIDE ADHESIVE FOR FIXING THE SORBENT LAYERS OF OVERPRESSURED, ONE-AND MULTILAYER-CHROMATOGRAPHIC PLATES AND A PROCESS FOR THE PREPARATION THEREOF

BACKGROUND OF THE ART

The present invention relates to a new adhesive eliminating the disadvantages of the adhesives used up to now for the preparation of TLC and HPTLC chromatographic plates and satisfying the special demands of the high pressure single-layer and multilayer chromatographic procedures.

The invention also relates to the preparation of the adhesive.

BACKGROUND OF THE INVENTION

Adhesives based on different compounds are used for the fixing of the adsorbent layers to the chromatographic plates, in classical thin-layer chromatography (TLC) and high-performance chromatography (HPTLC). The most preferable adhesives are those which are resistant against aggressive reagents and are relatively inert.

One group of conventional adhesives (e.g., agar-agar, starch, polyvinyl alcohol, polyvinyl acetate) is sensitive to aggressive reagents; furthermore they partially dissolve in systems containing water in higher amounts whereby their use is limited (German Patent Specification No. 1,442,456 and Hungarian Patent Specification No. 161,267).

Instead of these adhesives inert organic polymeric or inorganic adhesives are used which are completey resistant to aqueous systems and organic solvents and partially resistant to different chemical reagents. According to the German Patent Specification No. 1,442,446 a polymer of high degree of polymerization, based either on acrylic or methacrylic acid or salts thereof or copolymers of ethylene and maleinic acid or salts thereof, is used as binding agent. The German Patent Specification No. 1,517,929 relates to the use of polyacrylamide and/or polymethacrylamide and the derivatives thereof for the fixing of adsorbent layers based on different organic or inorganic materials. According to the German Patent Specification No. 1,915,963 an alkaline metal silicate is used as binding agent. These organic base adhesives have the disadvantage that they are not always resistant to especially agressive reagents (e.g. sulphuric acid), particularly at higher developing temperatures, further they decolorize and react with important reagents such as ninhydrine to such a great extent that this side-reaction makes quantitative evaluation difficult. When an alkaline metal silicate adhesive is used, the standard conditions can be assured only with considerable difficulty.

Due to these drawbacks these adhesives are not suitable for the preparation of HPLC chromatographic plates which have to satisfy the following demands:

(1) In high pressure single layer and multilayer chromatographic methods the solvent mixture migrates due to the flow induced by e.g. a Thus there is a possibility of use of viscous solvent mixtures such as aqueous buffers. The adhesive and the sorbent layer fixed with said adhesive must resist these aqueous viscous mixtures and cannot become unstuck, cannot upwarp etc.

(2) Moreover, a chromatographic plate with a sorbent layer is also exposed to a significant external pressure in a pressurized ultramicro chamber, thus the adhesion of the sorbent layer has to withstand this pressure as well.

(3) The reduced sensitivity of the adhesive to the reaction with ninhydrine is especially important as the high pressure single layer and multilayer chromatography is very much preferred for the quantitative analysis of the amino acids and peptides. The importance of the detection of amino acids of trace amounts, e.g. $N^\epsilon$-methylated lysines, has to be stressed because the spots of the said amino acids eventually cannot be seen in the back-ground.

(4) The fine-particle sorbent layers with a narrow particle size distribution based on different organic or inorganic compounds, have to be fixed close to each other and the adhesion of adsorbent layers based on a mixture of organic and inorganic compounds also has to be safely solved. The different features of the materials, e.g. the different swelling capacity should not influence the quality of the adhesion.

(5) A great advantage of overpressured one- and multilayer chromatography is that especially fine-particle (e.g. 3–5 $\mu$m) and thin-film-like (e.g. 45 $\mu$m thick) sorbent layers can be also used. The adhesive must be suitable for the fixing of such sorbents as well.

(6) A basic demand of high pressure single layer and multilayer chromatography is that regardless of the particle size sorbent layers could be used which particle size is in a narrow range, as due to the forced flow of the solvent the irregular local flow among the particles of the sorbents of significantly different particle size range results in an increased longitudinal diffusion. The fixing of said sorbents is more difficult than that of sorbent particles of different size but the appropriate adhesive has to satisfy this demand as well.

(7) One of the disadvantages of chromatographic plates with a sorbent layer opposite a column packings is in that the presence of the adhesive results in the decrease of the effectiveness of the development and especially the authenticity of the quantitative evaluation.

(8) Finally, temperature plays a very important role in the separation efficiency of high pressure single layer one- and multilayer chromatographic methods. The optimum temperature depends on the features of the systems, the best temperature can be either high or low. Such an adhesive should be preferably used which can reliably fix the sorbent layer to a suitable carrier plate, e.g. aluminum foil, and to a cover sheet, e.g. teflon, between the temperature range of +5° and +120° C.

SUMMARY OF THE INVENTION

The present invention provides an adhesive based on polyacrylamide and a method of the preparation thereof, said adhesive being suitable for the appropriate fixing of fine-particle sorbent layers, especially which particle size is in a narrow range, and mixtures thereof. Said layers can consist of organic (cellulose, artificial polyamide resins) and/or inorganic (e.g. silica gel, aluminum oxide, with chemically bound or unbound nonpolar phase supplied silica gel) compounds, and said sorbent layers are deposited on chromatographic plates used in overpressured layer chromatographic apparatuses.

DETAILED DESCRIPTION OF THE INVENTION

The invention is based on the recognition that the adhesive activity of polyacrylamides prepared by different manners to adsorbents is different and depends on the quantity and quality of the matrix forming monomers and the temperature of the polymerization. The monomers and oligomers remaining in the gel matrix have a detrimental influence on the efficiency and indifferent surface features of the polyacrylamide based adhesives, therefore they have to be removed.

It has also been recognized that the fraction suitable for the fixing of the sorbent layer can be precipitated from the homogenized gel matrix prepared in a controlled temperature range, by the aid of a water soluble organic solvent, preferably acetone, and thus the desired fraction can be separated from the monomers and oligomers having a disadvantageous influence on the characteristic features of the adhesive.

The adhesive according to the invention is prepared by forming a polyacrylamide gel matrix of special composition in a controlled temperature range, thereafter precipitating a fraction by the aid of a solvent, homogenizing it in water and recovering the polyacrylamide adhesive free of monomers and oligomers by further precipitations and homogenizations.

The polyacrylamide gel adhesive is suitable for the fixing of one- and multilayer chromatographic sorbent layers. The density of the adhesive is within the range of 1.004 to 1.008 g./ml., its viscosity is $2 \leq \eta_{rel} \leq 20$. The adhesive is insoluble in the majority of the usual solvents, is water resistant, resists to agressive reagents (e.g. sulphuric acidic vanilline) and is not sensitive to ninhydrine. The sorbent layers fixed with this adhesive preserve their shape. The adhesive does not react even at higher internal and external chamber pressures and at higher developing temperatures. It can be also used for fixing of fine-particle organic and/or inorganic sorbents whose particle size is in a narrow range or mixtures thereof.

The adsorbent layers fixed with the adhesive according to the invention far more satisfy the quantitative evaluation than the adsorbent layers prepared by the aid of known and widely used adhesives.

According to the process of the invention to an aqueous solution of acrylamide and N,N'-methylene-bis-acrylamide N,N,N',N'-tetramethyl ethylene diamine (TEMED) and then another catalyst, preferably ammonium peroxydisulphate are added at 21°–30° C., then the polyacrylic amide gel thus obtained is homogenized in a homogenizer. Thus, an opaline solution is obtained which is treated with a water soluble solvent, preferably acetone. A curdy precipitate is obtained which is then freed from solvent and again pulpified by adding the original amount of water. The latter operation can be repeated several times. The opaline aqueous solution obtained after the pulpification of the last curdy precipitate is the solution of the adhesive of the invention.

The preferred embodiments of the process of the invention are as follows:

A very preferred embodiment of the process uses as starting material an aqueous solution containing 2.0% of acrylamide and 0.8% of N,N'-methylene-bis-acrylamide is used.

It is preferred to use N,N,N',N'-tetramethyl ethylene diamine (TEMED) together with ammonium peroxydisulphate [$(NH_4)_2S_2O_8$] as catalysts but other catalyst pairs can be also used, e.g. $(NH_4)_2S_2O_8$ with 3-dimethylamino propionitrile or riboflavine with TEMED.

TEMED is directly added to the reaction mixture while ammonium peroxydisulphate is dissolved in some milliliters of water and poured into the very center of the solution previously stirred up very intensively. The self-mixing automatically stops. Ammonium peroxydisulphate can be also added in solid form to the solution stirred up. The self-mixing ceases in this case as well. The solution starts to become opaline after 4–5 minutes and this process ceases after 30 minutes in general.

The temperature of the gelation should suitably start at 22°–23° C. and rises to a maximum temperature of 28°–30° C.

The solidified gel is pulpified for 5 sec. in a Waring-type blendor, whereafter the liquid opaline solution is suitable for the solvent fractionation.

From the opaline, pulpified solution the valuable large molecules can be precipitated by the addition of a water soluble solvent such as acetone, methanol, ethanol etc. while the smaller molecules are retained in the solution. Preferably acetone is used as solvent and in this case the most preferable volume ratio of the opaline solution and the acetone is 1:1.

The curdy precipitate precipitated by acetone is pulpified with water preferably for 30 sec. in every case. Upon adding of acetone heat evolves, therefore the solution is decanted under cooling.

The more precipitation is carried out, the better the quality of the adhesive is, but suitably three precipitations are carried out.

The polyacrylamide content of the opaline adhesive solution varies within 1.6 and 2.2%. Knowing this data the necessary percentual amount of the adhesive applied to the sorbent layer can be calculated and is generally between 0.5 and 5.0%.

The invention is illustrated by the aid of the following, non-limiting examples.

EXAMPLE 1

(A) Preparation of polyacrylamide adhesive 20 g. of acrylamide and 8 g. of N,N'-methylene-bis-acrylamide are dissolved in 1000 ml. of distilled water. Then 3 ml. of TEMED are added and the aqueous solution the temperature of which is set to 22.5 C.° is agitated thoroughly in one direction and 0.8 g. of $(NH_4)_2S_2O_8$ dissolved in 3 ml. of water are poured to the center of the stirred solution. After 4 minutes the mixture starts to become opaline while the temperature rises to 29 C.° and after 30 minutes the gelation ends.

The gel is pulpified for 5 sec. in a Waring-type blendor and 1000 ml. of acetone are added to the 1000 ml. of opaline solution. The solution is decanted under cooling, the curdy precipitate is collected with the precipitate impacted to the walls of the vessel by the aid of aliquots of 1000 ml. of distilled water and pulpified for 30 sec. To the opaline solution thus obtained further 1000 ml. of acetone are added, the previous operation is repeated, i.e. a further precipitation is carried out by the aid of acetone. (The solutions achieved in the course of decantation are always poured out).

The polyacrylamid content of the 1000 ml. of opaline solution obtained in the last step is 0.021 g./ml. with a density of 1.004 g./ml. and a $\eta_{rel}$ of 4.65.

(B) Preparation of the adsorbent layers

To 44 g. of silica gel (average particle size: 6 μm); inside diameter: 90 Å/57 ml. of adhesive solution diluted with 87.5 ml. of water (concentration: 2.7%, calculated for the silica gel) are added. The pulp thus obtained is carefully stirred and thereafter pulpified for 60 sec. in a Waring-type blendor. The thus-obtained pulp of sour creme consistency as spread continously to an 0.1 mm. thick sheet of aluminium foil in a thickness of 0.2 mm, thus a layer with a thickness of 0.16 mm. is obtained after drying. Having cut the edges 7 pieces of chromatographic plate of 20 cm. width and 20 cm. length are obtained.

(C) Overpressured one-layer chromatographic development

From one of the chromatographic plates prepared according to the previous point (B) the sorbent layer is removed in 5 mm width at three edges and by the aid of a polymer dispersion solution containing polyvinyl acetate and polyacrylamide a water and solvent resistant polymeric film is formed. 15 identical samples of CAMAG II color test agent were applied at 3.0 cm from the impregnated edge, 9-9 mm from each other. After the sampling spots are dried, the chromatographic plate is placed to CHROMPRES 10-type pressurized ultramicro chamber provided with an insert plate made of teflon, in which channels are shaped up for directing the solvent. The cushion pressure is 1.2 MPa, the flow rate of the solvent is 185 ml./h. the developing time is 4.6 minutes, and methylene chloride is used as solvent. On evaluating the chromatogram thus obtained a deviation of ±1.5% could be observed in case of each of the colors.

(D) Highpressure four-layer chromatographic development

Four of the chromatographic plates with adsorbent layer prepared according to the previous point (B) are impregnated at three edges by a polymer dispersion solution containing a polyvinyl acetate and polyacrylamide through heating this treated plates at 100 C.° for 10 minutes. The upper three of the four plates impregnated at the edges are perforated by a 185-mm-long, 2-mm-wide slit, 15 mm from the anticipated odd edge of the impregnated part of adsorbent layer.

Onto three perforated plates with adsorbent layer prepared by the same manner an extract of a drop of 3×15 samples of chamomille flowers are applied in aliquot amounts at a 15 mm distance from the perforated slit and of 9-9 mm. from each other. After the spots of the sample are dried, the sheets are precisely superimposed on one another. The lowest sheet is unperforated, but its edges are impregnated and samples of the extract of 15 other camomille flower drops are applied onto it. The system thus obtained is placed into a pressured CHROMPRES 10-type ultramicro chamber. Benzene is used as eluent. Cushion pressure: 1.1 MPa. Developing time: 16.2 minutes. After development the plates are set apart, dried, sprayed with a 90% solution of sulphuric acid containing 0.2% of vanilline, heated at 105 C.° for 5 minutes and evaluated visually and by chromatogram spectrophotometer. The front distances and the $R_f$ values are the same on the different sheets, the standard deviation is within the allowed range.

EXAMPLE 2

Chromatographic plates with silica gel adsorbent layer prepared according to Example 1 were cut into 20×40 cm. pieces. The adsorbent layer was removed from the opposite sides in a width of 5-5 mm. and on these sites water and solvent resistant polymeric film was formed, said chromatographic plate being suitable for two-directional high pressure thin-layer chromatography. A channel was formed in the center of the adsorbent layer in a width of 180 mm. for leading the solvent, whereafter 15-15 samples of different wheat seed protein hydroliates were applied onto the plate in aliquot amounts, on both sides of the channel in a distance of 15 mm. and in a distance of 9 mm. from each other. After sampling the spots were dried, the plates were placed to a CHROMPRES 10-type ultramicro chamber. Cushion pressure: 1.2 MPa. Eluent: a 4:1:1 mixture of n-butanol/glacial acetic acid/water. Developing time: 68 minutes.

After development the dried adsorbent layer was sprayed with a 0.2% solution of ninhydrine prepared with a mixture of methanol and acetic acid and saturated with cupric sulphate, then heated and the color chromatogram was evaluated by spectrophotometer.

EXAMPLE 3

The following adsorbent layer was prepared by the aid of the adhesive prepared according to Example 1:

40 g. of talc (average particle-size: 3-4 μm) were pulpified with 40 ml. of adhesive solution diluted with 40 ml. of distilled water in a Waring-type blender for 75 sec. The pulp of sour cream consistance thus obtained was applied in a layer of 0.15 mm. thickness onto a 0.15-mm.-thick sheet of polyterephthalate foil, thus after drying a 0.1-mm.-thick talc layer was obtained. Having cut the edges 6 pieces of 20×20 cm. chromatographic plate were obtained. The adsorbent layers were removed in 5 mm. width at three edges of the chromatographic plates thus obtained and water and solvent resistant polymeric film was formed on these stripes by the aid of a polymer dispersion containing polyvinyl acetate and polyacrylamide. To one of the sheets with impregnated edges Digitalis extracts and authentic Digitalis heart glycosides dissolved in a mixture of methanol and chloroform in aliquote amounts were applied. The sheet was placed into a CHROMPRES 10-type ultramicro chamber. A 18:85 mixture of methyl ethyl ketone and water was used as eluent. Development time: 25 minutes.

After drying the adsorbent layer was sprayed with 20% aqueous phosphoric acid, heated at 120 C.° for 20 minutes. Greenish yellow spots were obtained which were quantitatively and qualitatively evaluated.

EXAMPLE 4

By the aid of the adhesive solution of Example 1 an adsorbent layer with concentration zone was shaped up in the following manner. To the bigger vessel of the special spreading head (with wider spreading surface) a suspension of 33 g. of silica gel of 6 μm. average particle size and 90 Å inside diameter and 43 ml. of the adhesive solution diluted with 66 ml. of distilled water (concentration: 2.7%, calculated for silica gel) was poured after appropriate pulpifying. To the smaller vessel (the spreading head is of smaller surface) a pulp of 11 g. of siliceous earth of 15 μm. average particle size and 15 ml. of the adhesive solution diluted with 21.5 ml. of water was added. The two pulps were applied to a 0.1-mm.- thick sheet of aluminum foil in a layer of 0.1 mm. thickness, thus 0.08-mm-thick adsorbent layer provided with a concentration zone was obtained after drying. The adsorbent layer consisted of a 4 cm. wide inactive siliceous earth stripe and a 16 cm. wide active, fine-particle silica gel stripe.

Having cut the edges, 10 sheets of 20×20 cm. were obtained and impregnated at the edges according to Example 1 in order to use in overpressured one layer chromatographic procedure. Camomille oil samples of different origin were separated on the adsorbent layer. The components of the samples (polyines, sesquiterpene alcohols) separated in the sharp bands.

EXAMPLE 5

By using the adhesive solution prepared according to Example 1 an adsorbent layer comprising silica gel and a resin was prepared. 28 g. of silica gel of 6 μm. average particle size and 10 g. of a strong cation exchange resin of 5–8 μm. average particle size were pulpified with 42.5+70 ml. of distilled water for 60 sec. The pulp was applied in a layer 0.2 mm. thick onto a 0.4-mm.-thick sheet of aluminium foil by continuous spreading, thus a 0.17-mm.-thick, smooth, pale yellow sorbent layer was obtained. Having cut the edges 7 pieces of a 20×20 cm. chromatographic plate with sorbent layer were achieved.

For using the sheets in high pressure single-layer and multilayer chromatographic procedures the edges of the plates were impregnated according to Example 1.

In order to verify the effectiveness of the plates with sorbent layer, hydrochloric acid hydrolizates of different plant peptides and authentic amino acid mixtures were applied to the layers. After drying the plate was placed to a CHOMPRES 10-type ultramicro chamber. Citrate buffer of 3.45 pH, as eluent was used while as developer a 0.2% solution of ninhydrine in a mixture of methanol and acetic acid was applied.

EXAMPLE 6

20 g. of acrylamide and 8 g. of N,N'-methylene-bis-acrylamide are dissolved in 1000 ml. of distilled water. To the mixture 2.8 ml. of TEMED are added, the temperature of the solution is set to 23 C.° and the solution is throughly stirred up with one-directional movements. Then 0.9 g. of crystalline (NH4)2S2O8 are poured to the center of the stirred solution. The opalization begins after 5 minutes, the total gelation comes to an end after 30 minutes.

The gel is worked up according to Example 1. An opaline adhesive solution with a density of 1.005 g./ml. and a viscosity of ηrel=6.8 was obtained.

By using the above adhesive an adsorbent layer was prepared in the following manner:

40 g. of silica gel of 3 μm. average particle size and 60 Å inside diameter were pulpified with 56 ml. of the adhesive solution diluted with 90 ml. of water in a Waring-type blender. The pulp was applied in a layer 0.1 mm. thick to a 0.1-mm.-thick sheet of aluminium foil by continous spreading, thus 0.06-mm.-thick adsorbent layer was obtained after drying. After cutting the edges and cutting the sheets to pieces, the sides of the chromatographic plates with adsorbent layer were impregnated according to Example 1 and the plates were used for testing color agents in an high pressure single-layer chromatographic system by applying rather small amounts of samples (e.g. 5–10 μg.) to the adsorbent layer.

EXAMPLE 7

The following chromatographic plate with adsorbent layer was prepared by the aid of the adhesives of Example 6:

40 g. of aluminium oxide of 10 μm. average particle size were pulpified with a mixture of 28 ml. of the adhesive and 39 ml. of water for 225 sec., thereafter the pulp was applied in a layer of 0.2 mm. thickness onto 20×20 cm., 2-mm.-thick glass sheets, thus a 0.6-mm.-thick aluminum oxide layer was obtained after drying.

The adsorbent layer of the chromatographic plates activated at 110 C.° was removed at three edges in 4-mm.-width and these stripes were covered by a polymeric film. Onto the so formed chromatographic plate alkaloid-containing purified extracts prepared from poppy and dissolved in an 1:1 mixture of methanol and chloroform were applied in aliquote amounts. After sampling the spots were dried, the sheets supplied with a suitable protecting plastic frame (in order to protect the water cushion system of the pressured ultramicro chamber against the cleaving effect of the edges of the glass sheets) were placed to a CHROMPRES 10 ultra-micro chamber of a cushion pressure of 1.2 MPa. A 40:50:10 mixture of heptane/chloroform/ether as eluent and Dragendorff reagent modified by Vágujfalvi as developer were used for the development of the alkaloids.

EXAMPLE 8

An adsorbent layer similar to the silica gel layer prepared according to Example 6 was formed by using the adhesive of Example 6 and a pulp containing 1.8% of zinc silicate UV indicator activated by manganese.

EXAMPLE 9

36 g. of acrylamide and 16.2 g. of N,N'-methylene-bis-acrylamide were dissolved in 2000 ml. of distilled water. Then 4 ml. of 3-dimethylamino propionitrile were added, the temperature of the solution was set to 22 C.° and the mixture was throughly stirred up by one-directional movements, 1.0 g. of (NH4)2S2O8 was quickly dissolved in 3 ml. of distilled water and this solution was poured to the center of the stirred mixture. The opalization started after 8 minutes and the complete gelation finished after 45 minutes.

The thus formed gel was worked up according to Example 1. An opaline adhesive solution of a density of 1.006 g./ml. and a viscosity of ηrel=4.3 was obtained.

By using the above adhesive the following sorbent layer is prepared: 30 g. of high purity cellulose of 5 μm. average particle size is mixed with 30 ml. of the adhesive diluted with 30 ml. of water and the pulp is applied in a layer 0.15 mm. thick onto a 0.9-mm.-thick sheet of aluminium foil by a conventional manner. The edges are cut and the sheets are cut up. The edges are impregnated and on the thusly formed sheets amino acids are tested in an overpressured one-layer chromatographic system, by using a 3:4:1:2 mixture of methyl ethyl ketone/acetonitrile/acetic acid/water eluent, at 1.4 MPa external cushion pressure in 59 minutes (in the case of overdevelopment).

EXAMPLE 10

The adhesive of Example 9 was used for the fixing of RP-18 type silica gel supplied with chemically bound stationary phase to a sheet of aluminium foil.

20 g. of C-18 type reverse phase silica gel powder are pulpified with 80 ml. of polyacrylamide adhesive and 60 ml. of isopropanol for 175 sec. The thin pulp thus obtained is applied in a layer 0.18 mm. thick onto a 0.12-m.-thick sheet of aluminum foil. After cutting into pieces and impregnating the edges the dried chromatographic plates are used in a CHROMPRES 10-type ultramicro chamber for the reversed phase separation of poppy alkaloids. A 6:4 mixture of acetonitrile and 0.005M of $KH_2PO_4$ solution are used as eluent, while Dragendorff reagent containing ethyl acetate is used as developer.

EXAMPLE 11

The following adsorbent layer was prepared by the aid of the adhesive of Example 9:

88 g. of silica gel of 5 μm average particle size and 60 Å inside pore diameter are pulpified with 135 ml. of the adhesive diluted with 175 ml. of water for 85 sec. in a Waring-type blender. The obtained pulp was applied in a layer 0.65 mm. thick onto a 11-mm.-thick sheet of degreased aluminum foil thus a 0.5-mm.-thick silica gel adsorbent layer was achieved.

On the thusly formed adsorbent layer the $N^\epsilon$-methylated lysines formed in the spontaneous methylation and formylation reaction of L-lysine and formaldehyde were separated with the use of distilled water as eluent, at 1.3 MPa cushion pressure.

What we claim is:

1. A process for preparing a polyacrylamide adhesive having a density of 1.004 to 1.008 g/ml of and a relative viscosity of $2 \leq \eta \leq 20$, suitable for the appropriate fixing of fine particle sorbent layers, based on organic or inorganic compounds, and supplied with a bound or unbound nonpolar phase, used in high pressure single layer and multilayer chromatographic procedures, which comprises the following steps:
   (a) polymerizing in an aqueous mixture, acrylamide and N,N-methylene-bis-acrylamide, in the presence of a catalyst, at 21° to 30° C., wherein the aqueous mixture contains 1.6 to 2.5% acrylamide and 0.6 to 1.0% N,N-methylene-bis-acrylamide repsectively to obtain a polyacrylamide gel;
   (b) homogenizing the polyacrylamide gel to obtain an opaline solution containing acrylamide-N,N-methylene-bis-acrylamide copolymer;
   (c) fractionally precipitating the acrylamide-N,N-methylene-bis-acrylamide copolymer from the opaline solution with a water-soluble solvent to obtain a curdy precipitate containing the desired fraction of the copolymer and a supernatant liquid containing undesired monomers and oligomers;
   (d) removing the curdy precipitate and pulpifying same by adding water to form again a homogeneous opaline solution; and
   (e) repeating steps (c) and (d) several times to obtain a homogenous opaline composition of the polyacrylamide adhesive.

2. A process as claimed in claim 1 which comprises using from 1.9 to 2.2% and from 0.8 to 1.0% aqueous solution of acrylamide and N,N'-methylene-bis-acrylamide, respectively.

3. A process as claimed in claim 1 which comprises using N,N,N',N'-tetramethylethylene diamine or 3-diethylamino propionitrile, each in combination with ammonium peroxydisulphate as catalyst.

4. A process as claimed in claim 1 which comprises starting the polymerization reaction preferably at 22 C°.

5. A process as claimed in claim 1 which comprises using ethanol, methanol or acetone for precipitating the desired fraction from the gel matrix.

6. A polyacrylamide adhesive having a density of 1.004 to 1.008 g/ml and a relative viscosity of $2 \leq \eta \leq 20$, suitable for the appropriate fixing of fine particle sorbent layers, based on organic or inorganic compounds, and supplied with a bound or unbound nonpolar phase, used in high-pressure single layer and multilayer chromatographic procedures, prepared by a process which comprises the following steps:
   (a) polymerizing in an aqueous mixture, acrylamide and N,N-methylene-bis-acrylamide, in the presence of a catalyst, at 21° to 30° C., wherein the aqueous mixture contains 1.6 to 2.5% acrylamide and 0.6 to 1.0% N,N-methylene-bis-acrylamide respectively to obtain a polyacrylamide gel;
   (b) homogenizing the polyacrylamide gel to obtain an opaline solution containing acrylamide-N,N-methylene-bis-acrylamide copolymer;
   (c) fractionally precipitating the acryalmide-N,N'-methylene-bis-acrylamide copolymer from the opaline solution with a water-soluble solvent to obtain a curdy precipitate containing the desired fraction of the copolymer and a supernatant liquid containing undesired monomers and oligomers;
   (d) removing the curdy precipitate and pulpifying same by adding water to form again a homogeneous opaline solution; and
   (e) repeating steps (c) and (d) several times to obtain a homogenous opaline composition of the polyacrylamide adhesive.

7. The adhesive of claim 6 prepared by using from 1.9 to 2.2% and from 0.8 to 1.0% aqueous solution of acrylamide and N,N'-methylene-bis-acrylamide, respectively.

8. The adhesive as claimed in claim 6 prepared by using N,N,N',N'-tetramethyl ethylene diamine or 3-diethylamino propionitrile, each in combination with ammonium peroxydisulphate as catalyst.

9. The adhesive as claimed in claim 6 prepared by starting the polymerization reaction preferably at 22 C.°.

10. An adhesive as claimed in claim 6 prepared by using acetone, methanol or ethanol for the precipitating of the desired fraction from the gel matrix.

* * * * *